(12) United States Patent
Valkoun et al.

(10) Patent No.: US 11,826,260 B2
(45) Date of Patent: Nov. 28, 2023

(54) EXPANDABLE INTERBODY SPACER (71) Applicant: Astura Medical Inc., Irving, TX (US)

(72) Inventors: Anthony Valkoun, Irving, TX (US); Thomas Purcell, Irving, TX (US)

(73) Assignee: ASTURA MEDICAL INC, Irving, TX (US)

( * ) Notice: Subject to any disclaimer, the term of this patent is extended or adjusted under 35 U.S.C. 154(b) by 0 days.

(21) Appl. No.: 17/841,611

(22) Filed: Jun. 15, 2022

(65) Prior Publication Data
US 2022/0395381 A1 Dec. 15, 2022

Related U.S. Application Data (60) Provisional application No. 63/210,943, filed on Jun. 15, 2021.

(51) Int. Cl.
*A61F 2/44* (2006.01)
*A61F 2/30* (2006.01)

(52) U.S. Cl.
CPC .... *A61F 2/442* (2013.01); *A61F 2002/30507* (2013.01); *A61F 2002/30556* (2013.01)

(58) Field of Classification Search
CPC ...... A61F 2/4455; A61F 2/446; A61F 2/4465; A61F 2/447; A61F 2002/30579; A61F 2002/30553; A61F 2002/30556; A61F 2002/30545; A61F 2002/30555; A61F 2002/30266
See application file for complete search history.

(56) References Cited

U.S. PATENT DOCUMENTS

| | | | |
|---|---|---|---|
| 9,351,848 B2 * | 5/2016 | Glerum | A61F 2/4611 |
| 2018/0193164 A1 | 7/2018 | Shoshtaev | |
| 2019/0307577 A1 * | 10/2019 | Predick | A61F 2/4455 |
| 2019/0388232 A1 | 12/2019 | Purcell et al. | |
| 2020/0352731 A1 | 11/2020 | Berry | |
| 2021/0121300 A1 * | 4/2021 | Weiman | A61F 2/442 |
| 2021/0137695 A1 | 5/2021 | Huang | |

OTHER PUBLICATIONS

International Search Report and Written Opinion in PCT Application No. PCT/US22/33695 dated Sep. 13, 2022.

* cited by examiner

*Primary Examiner* — Eduardo C Robert
*Assistant Examiner* — Michelle C Eckman
(74) *Attorney, Agent, or Firm* — Michael R. Shevlin (57) ABSTRACT

An expandable interbody spacer for placement between adjacent vertebrae having two or more upper and lower endplates and lateral expansion wedges configured to couple a drive means to expand both a height and a width of the expandable interbody spacer from a collapsed state to an expanded state.

20 Claims, 5 Drawing Sheets

EXPANDABLE INTERBODY SPACER

CROSS-REFERENCE TO RELATED APPLICATIONS

This application claims the benefit of U.S. Provisional Application No. 63/210,943 filed Jun. 15, 2021, which is incorporated herein by reference.

FIELD

The present invention relates generally to the field of surgery, and more specifically, to an expandable intervertebral body fusion device (i.e., "interbody spacer") for placement in intervertebral space between adjacent vertebrae.

BACKGROUND

A spinal disc can become damaged as a result of degeneration, dysfunction, disease and/or trauma. Conservative treatment can include non-operative treatment through exercise and/or pain relievers to deal with the pain. In surgical treatments, interbody spacers may be used between adjacent vertebra, resulting in spinal fusion of the adjacent vertebra. Treatment options include disc removal and replacement using an interbody spacers such as anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

A fusion is a surgical method wherein two or more vertebrae are joined together (fused) by way of interbody spacers, sometimes with bone grafting, to form a single bone. The current standard of care for interbody fusion requires surgical removal of all or a portion of the intervertebral disc. After removal of the intervertebral disc, the interbody spacer is implanted in the interspace.

Interbody spacers must be inserted into the intervertebral space in the same dimensions as desired to occupy the intervertebral space after the disc is removed. This requires that an opening sufficient to allow the interbody spacer must be created through surrounding tissue to permit the interbody spacer to be inserted into the intervertebral space. In some cases, the intervertebral space may collapse prior to insertion of the interbody spacer. In these cases, additional hardware may be required to increase the intervertebral space prior to insertion of the implant.

In addition, minimally invasive surgical techniques may have been used on the spine. Under minimally invasive techniques, small incisions are done to access the intervertebral space. Through these incisions, discs are removed and an interbody spacer is placed in the intervertebral disc space to restore normal disc height. Minimally invasive spine surgery offers multiple advantages as compared to open surgery. Advantages include: minimal tissue damage, minimal blood loss, smaller incisions and scars, minimal post-operative discomfort, and relative quick recovery time and return to normal function.

Typical expandable implants utilize angled ramps in conjunction with slots or t-rails and a separate drive screw to compress the mechanism and force expansion. This type of mechanism limits the available expansion of the implant due to the amount of material required to house the slots or t-rails. Typically, the expansion ramp is not able to pass the midline of the part. In addition, this mechanism is typically limited to a single plane of expansion (I.E., height or width).

Current expandable implants are typically expensive and difficult to manufacture due to the complexity of the expansion mechanism and the available manufacturing techniques require the size and positional tolerance of these features to be relatively loose to allow for manufacturability. In addition, this type of mechanism limits the available expansion of the interbody spacer due to the amount of material required to house the slots and/or t-rails.

It would be desirable to develop an easy to manufacture expandable interbody spacer that can be inserted into the intervertebral space at a first smaller dimension and once in place, deploy to a second, larger dimension.

SUMMARY

Disclosed is an expandable interbody spacer that is configured to have an initial collapsed state having a first height and first width suitable for being inserted into an intervertebral space defined by a pair of adjacent vertebrae, and a final expanded state having a second height and second width that is greater than the first height. The expandable interbody spacer may be expanded from the initial collapsed state to the expanded state in-situ. The expanded state increases the distance between the adjacent vertebrae and provides support to the adjacent vertebrae while bone fusion occurs and also provides rigid support between the adjacent vertebrae that withstands compressive forces. By inserting the expandable interbody spacer into the intervertebral space in the initial collapsed state, it is possible to perform the surgery percutaneously with minimal disruption to tissues surrounding the surgical site and intervening soft tissue structures.

Increased height expansion for given implant size, width expansion and lordosis change in conjunction with height expansion. Expandable interbody spacers are typically limited in expansion capability at smaller footprints due to a limitation of available material, in addition they typically expand in a single plane (I.E. Height). Also, expandable implants are typically expensive and difficult to manufacture due to the complexity of the expansion mechanism.

DETAILED DESCRIPTION

The interbody spacer disclosed may be used for anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF). The expandable interbody spacer includes a collapsed state and expanded state. The collapsed state allows insertion between the adjacent vertebrae with minimal dimensions. The expandable interbody spacer expands both vertically and horizontally by means of single-angle ramps and rails. Upper and lower endplates single-angle ramps and rails to move the upper and lower endplates both horizontally and vertically away from each other. The endplates may also be textured to promote bony integration.

Figure 1:
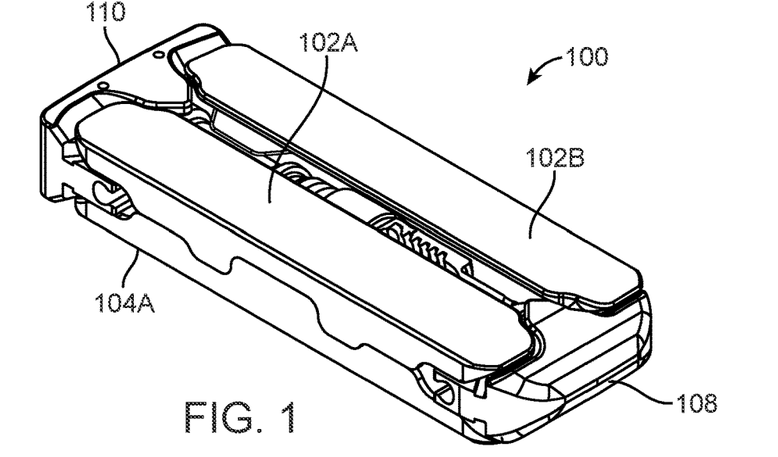
FIG. 1 is a perspective view of an expandable interbody spacer in a collapsed state for introduction into disc space.

FIG. 1 is a perspective view of an expandable interbody spacer 100 that consists of 13 primary components, including: a frame, a housing, two upper endplates, two lower endplates, right and left lateral expansion wedges, two proximal and two distal vertical expansion shuttles, and a drive screw. The frame and housing both contain single-angle ramps intended to induce lateral expansion of the right and left lateral expansion wedges. The four endplates contain single-angle rails intended to mate with the proximal and distal vertical expansion shuttles. The proximal and distal vertical expansion shuttles are captured within the lateral expansion wedges and contain a D-rail profile that mates with either the frame or shuttle.

By utilizing single-angle rails in conjunction with 'stacking' the mechanism, the expandable interbody spacer 100 is able to achieve significantly more rail engagement while also adding additional vertical support elements to the endplates in the expanded state. In addition, the utilization of L-rails in a staggered configuration allows for the expansion mechanism to exceed the midline of the part, this additional ramp length allows for increased implant expansion beyond what is typically available for any given implant footprint.

The expandable interbody spacer 100 also allows for a variation of angles for the Anterior/Posterior vertical expansion shuttles and respective Anterior/Posterior endplates. Via the varying of this angle one is able to induce different rates of vertical expansion of the distal and proximal ends of the endplates while maintaining symmetrical lateral expansion. The varying vertical expansion rate can be utilized to induce lordosis within the implant as it is expanded.

Referring again to FIG. 1. the expandable interbody spacer 100 is shown in a collapsed state having right and left upper endplates 102A, 102B, right and left lower endplates 104A, 104B, right and left lateral expansion wedges 106A, 106B, a frame 108 and a housing 110. The frame 108 is positioned on a distal end of the expandable interbody spacer 100 and the housing 110 is positioned on a proximal end of the expandable interbody spacer 100.

Figure 2:
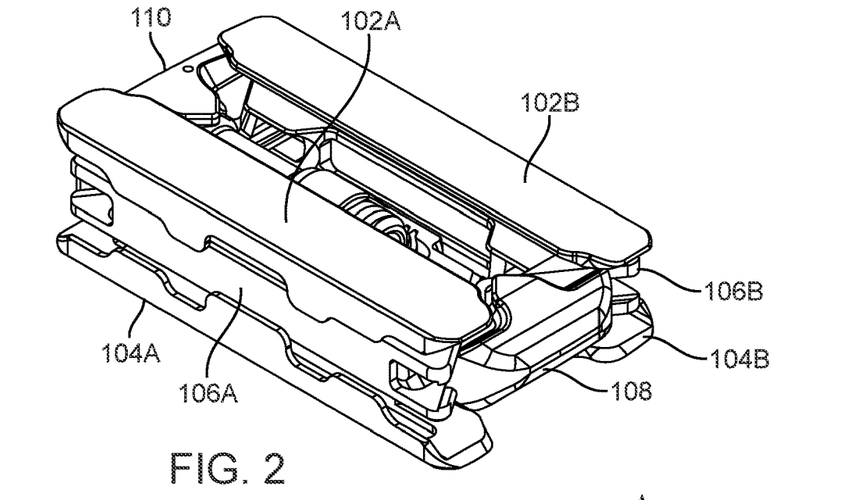
FIG. 2 is a perspective view showing the expandable interbody spacer of FIG. 1 in an expanded state.

FIG. 2 is a perspective view of the expandable interbody spacer 100 in an expanded state. During expansion, the expandable interbody spacer 100 expands both vertically and horizontally, changing the height H and width W from a collapsed state to expanded state. Changing the height H and width W includes the right and left upper endplates 102A, 102B and right and left lower endplates 104A, 104B simultaneously expanding both vertically and horizontally from each other, and the right and left lateral expansion wedges 106A, 106B expanding horizontally from each other.

During vertical expansion, the right and left upper endplates 102A, 102B and the right and left lower endplates 104A, 104B expand vertically V from each other. During horizontal expansion, the right upper and lower endplates 102A, 104A on one side expanded horizontally H1 from the left upper and lower endplates 102B, 104B on the other side, and the right and left lateral expansion wedges 106A, 106B expand horizontally H2 away from each other.

Figure 3:
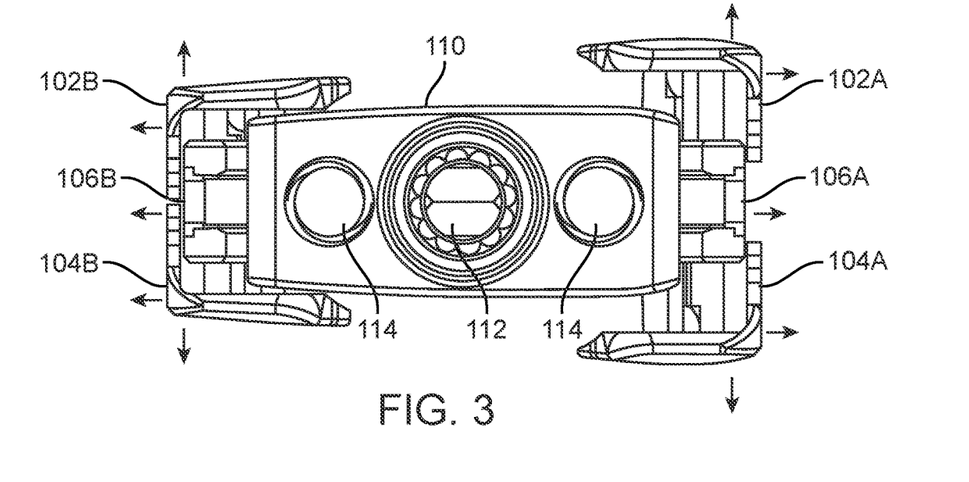
FIG. 3 is a proximal view of the expandable interbody spacer.

FIG. 3 is a proximal view of the expandable interbody spacer 100 in the expanded state with the right and left upper endplates 102A, 102B and the right and left, lower endplates 104A, 104B expanded both vertically and horizontally from each other, and the right and left lateral expansion wedges 106A, 106B expanded horizontally away from each other, and the housing 110. Also shown is a drive screw 112 coupled to the housing 110 and one or more holes or threaded bores 114 configured to engage one or more tools for implantation of the expandable interbody spacer 100.

Figure 4:
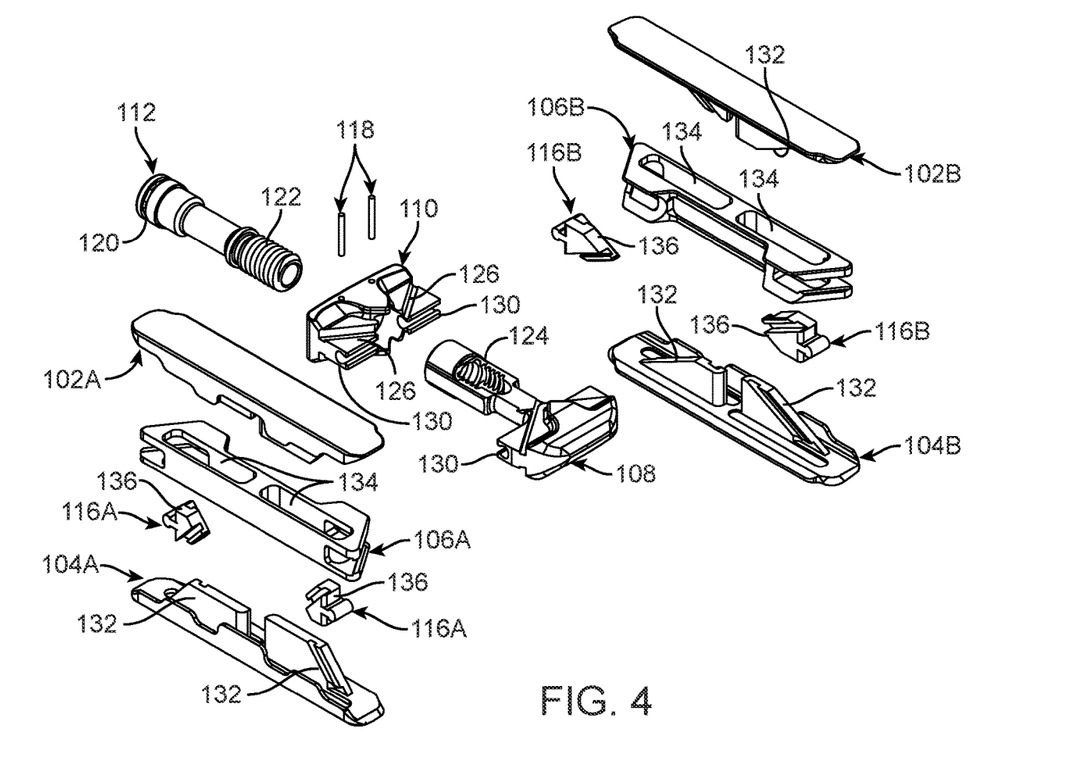
FIG. 4 is an exploded perspective view of the distal end of the expandable interbody spacer in the expanded state.

FIG. 4 is an exploded perspective view of the expandable interbody spacer 100 showing the components, including the right and left upper endplates 102A, 102B, the right and left lower endplates 104A, 104B, right and left lateral expansion wedges 106A, 106B, the frame 108, the housing 110, and the drive screw 112. Also shown are right and left vertical expansion shuttles 116A, 116B, and retention pins 118.

The drive screw 112 having a proximal end with a proximal slot 120 configured to receive retention pins 118 and a distal threaded portion 122 on a distal end configured to couple with a threaded portion 124 of the frame 108.

The frame 108 and the housing 110 include two angled ramps 126, 128 configured to interact with angled ramp ends of the right and left lateral expansion wedges 106A, 106B during expansion. In some embodiments, the angled ramps are single-angle ramps configured to induce lateral expansion of the right and left lateral expansion wedges 106A, 106B.

The frame 108 and the housing 110 further include lateral slots 130 configured to engage D-rail profile protrusions on the right and left vertical expansion shuttles 116A, 116B for lateral expansion.

The right and left upper and lower endplates 102A, 102B, 104A, 104B include ramped features 132 that fit through upper and lower openings 134 in the right and left lateral expansion wedges 106A, 106B. The ramped features 132 are configured to engage corresponding ramps 136 on right and left vertical expansion shuttles 116A, 116B. In some embodiments, the ramped features 132 and vertical expansion shuttle ramps 136 are single-angle rails that induce vertical expansion of the right and left upper and lower endplates 102A, 102B, 104A, 104B.

The vertical expansion shuttles 116A, 116B. are captured within inward facing slots 138 of the lateral expansion wedges 106A, 106B proximate the upper and lower openings 134.

Figure 5:
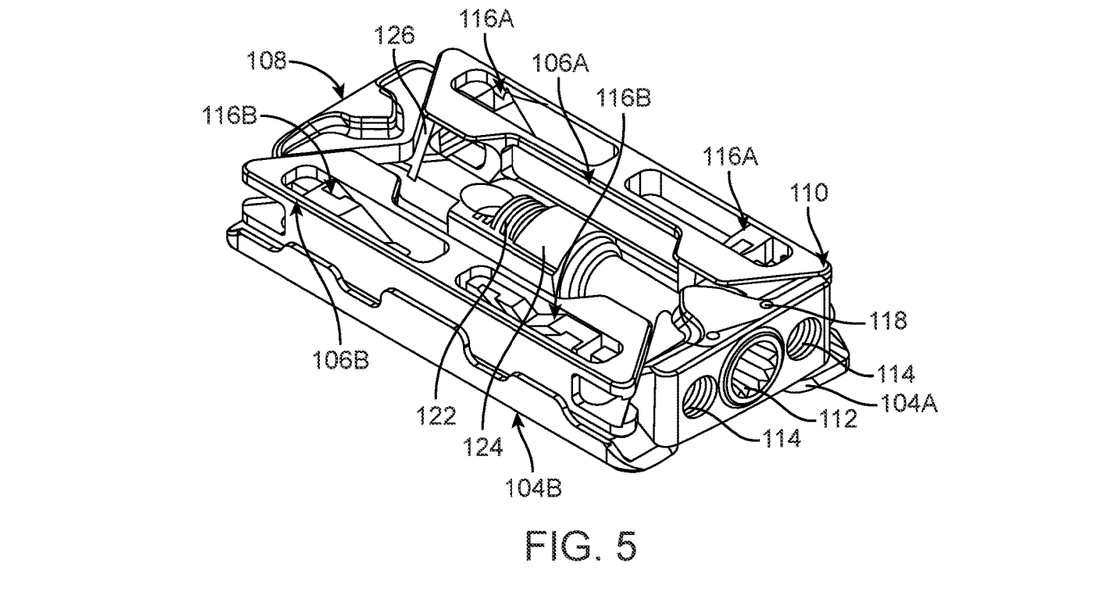
FIG. 5 is a perspective proximal view showing the assembled expandable interbody spacer without the upper endplates.

FIG. 5 is a perspective proximal view showing the assembled expandable interbody spacer 100 without the upper endplates 102A, 102B. In the embodiment shown, the proximal end of the drive screw 112 is positioned within the housing 110 and the retention pins 118 engage the slot 112. The threaded portion 112 on the distal end of the drive screw 112 is coupled to the threaded portion 124 of the frame 108.

The right and left vertical expansion shuttles 116A, 116B are captured within the lateral expansion wedges 106A, 106B and the ramped features 132 of the upper and lower endplates 102A, 102B, 104A, 104B are positioned within the upper and lower openings 134. The right and left vertical expansion shuttles 116A, 116B are engaged with the lateral slots 130 of the frame 108 and housing 110, and the ramps 136 are engaged with the ramp features 132 of the upper and lower endplates 102A, 102B, 104A, 104B.

Referring back to FIG. 2, the frame 108 and housing 110 are positioned relative to each other via the lateral expansion wedges 106A, 106B and the drive screw 112. Advancing the drive screw 112 in a first direction causes the frame 108 and housing 110 to translate towards each other. This translation forces the angled ramp ends of the lateral expansion wedges 106A, 106B to interact with the angled ramps 126, 128 on the frame 108 and housing 110, forcing lateral expansion of the lateral expansion wedges 106A, 106B, the vertical expansion shuttles 116A, 116B and upper and lower endplates 102A, 102B, 104A, 104B. During lateral expansion, the lateral expansion wedges 106A, 106B, vertical expansion shuttles 116A, 116B, and upper and lower endplates 102A, 104A, 102B, 104B expand away from each other.

Simultaneously, as the frame 108 and housing 110 axially translate toward each other, the vertical expansion shuttles 116A, 116B axially translate toward each other, inducing vertical expansion of the upper 102A, 102B endplates and lower endplates, 104A, 104B away from each other via the ramp 136 and ramp feature 132 interface between the vertical expansion shuttles 116A, 116B and upper and lower endplates 102A, 102B, 104A, 104B.

When the drive screw 112 is rotated in a second direction, the frame 108 and housing 110 move away from each other and the right and left components move toward each other, going from an expanded state to a collapsed state.

Figure 6A:
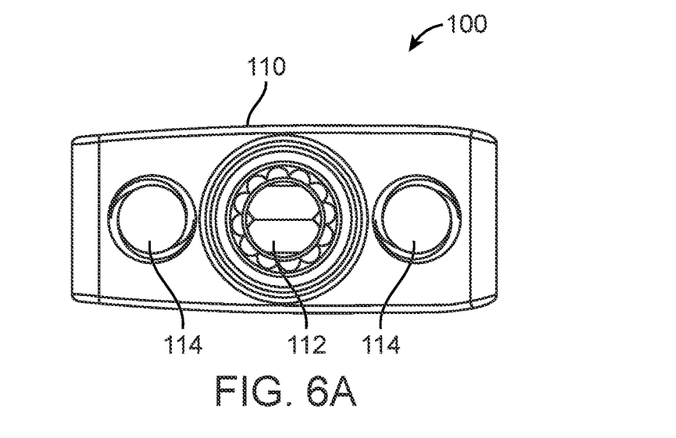
FIGS. 6A-6C show a proximal end view, a side view and a top view of the expandable interbody spacer of FIG. 1 in the collapsed state.

FIG. 6A is a proximal end view of the expandable interbody spacer 100 in the collapsed state showing the housing 106, the drive screw 108, and guide rod 110.

Figure 6B:
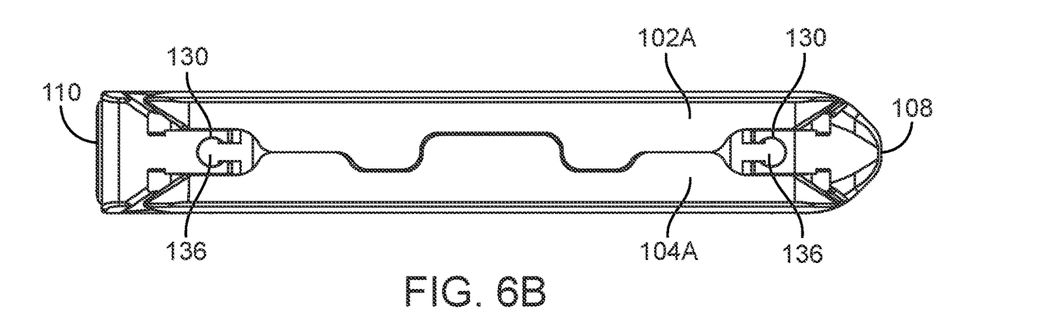

FIG. 6B is a side view of the expandable interbody spacer 100 in the collapsed state showing the upper and lower endplates 102A, 104A, the frame 104 and housing 106. Also shown are the single-angle ramps 124 on the top and bottom endplates 102A, 104A engaging the single-angle ramps 126 on the frame 104 and housing 106.

Figure 6C:
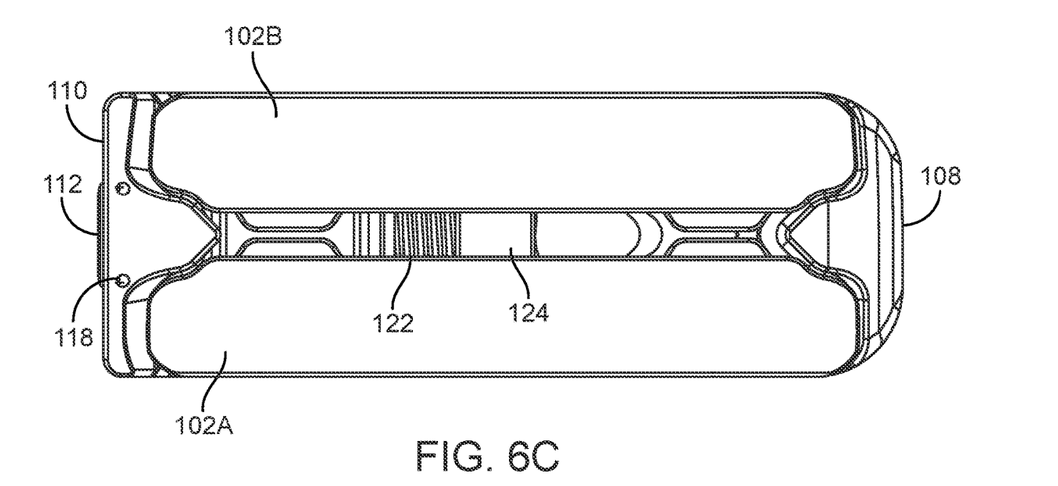

FIG. 6C is a top view of the expandable interbody spacer 100 in the collapsed state showing the upper endplates 102A, 102B and the rails 120.

Figure 7A:
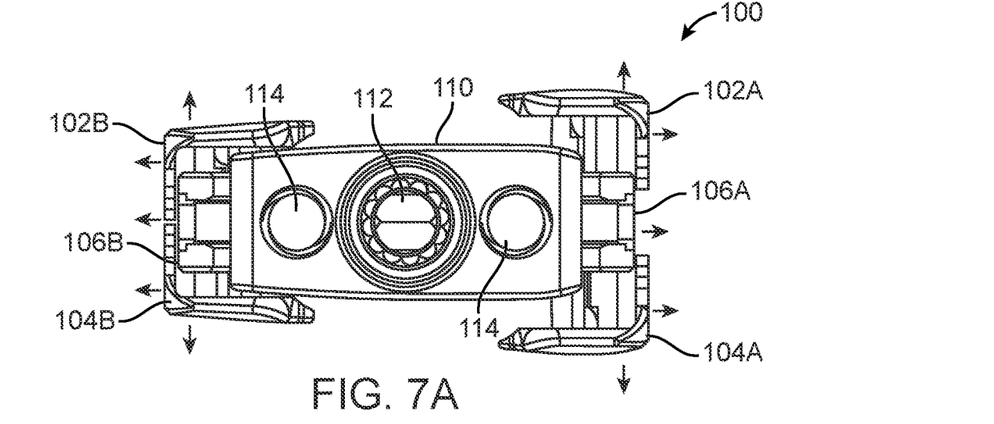
FIGS. 7A-7C show a proximal end view, a side view and a top view of the expandable interbody spacer of FIG. 1 in the expanded state.

FIG. 7A is a proximal end view of the expandable interbody spacer 100 in the expanded state showing the housing 110 with the drive screw 112, and the upper endplates 102A, 102B and lower endplates 104A, 104B moved in the vertical V away from each other, and the upper and lower endplates 102A, 104A and lateral expansion wedge 106A on one side and the upper and lower endplates 102B, 104B and lateral expansion wedge 106B on the other side moved in the horizontal H direction away from each other.

Figure 7B:
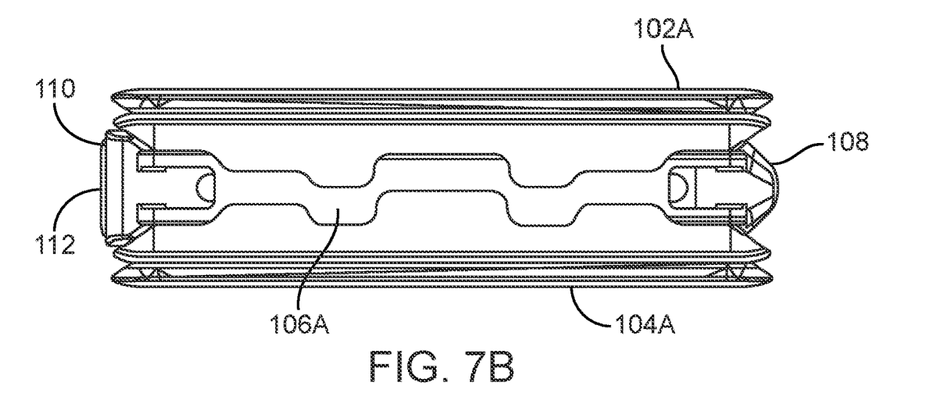

FIG. 7B is a side view of the expandable interbody spacer 100 in the expanded state showing the upper and lower endplates 102A, 102B, the frame 108 and housing 110.

Figure 7C:
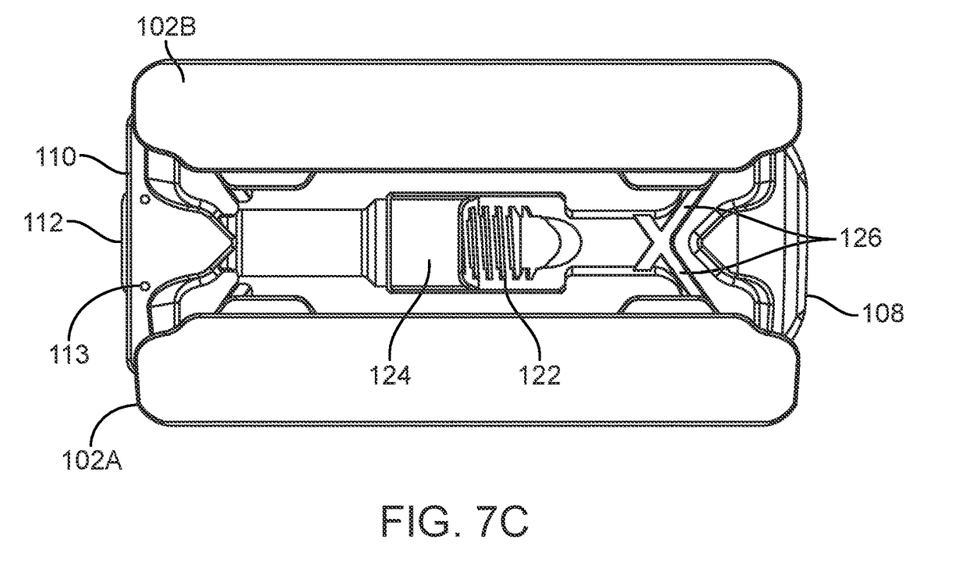

FIG. 7C is a top view of the expandable interbody spacer 100 in the expanded state showing the upper endplates 102A, 102B away from each other, the thread portion 122 of the drive screw 112 engaged with threaded portion 124 of the frame 108. Also shown are the angle ramps 126 on the frame 108 and housing 110.

While a drive screw is shown, the drive mechanism can be any mechanism capable of moving the frame and housing toward or away from each other or to expand or collapse the expandable interbody spacer. Other types of drive mechanisms may include: a belt drive, rack and pinion drive, linear motor drive, ball screw drive, lead screw drive, or any other suitable drive.

While two upper endplates, two lower endplates and two lateral expansion wedges are in the embodiments shown, other embodiments may include two or more upper endplates, two or more lower endplates or lateral expansion wedges. For example, there may be three upper and lower endplates and lateral expansion wedges, four upper and lower endplates and lateral expansion wedges, etc.

Figure 8A:
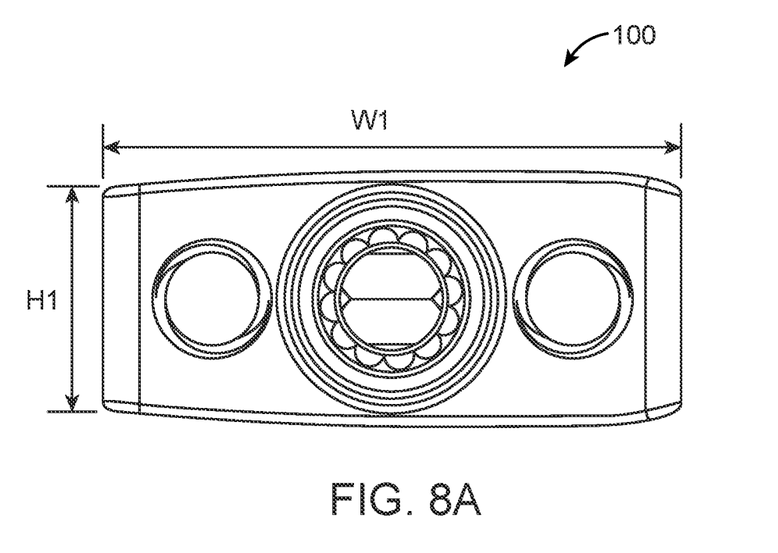
FIGS. 8A and 8B are proximal or front views of the expandable interbody spacer in collapsed and expanded states.
Figure 8B:
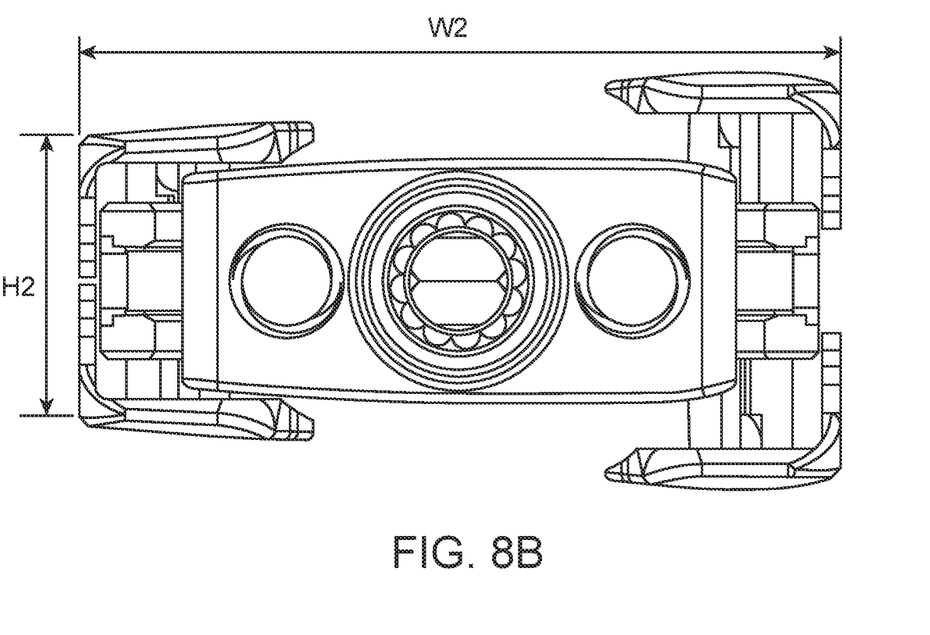

FIGS. 8A and 8B are proximal views of the expandable interbody spacer 100 in collapsed and expanded states. When the drive screw 112 is turned or rotated in the first direction, the frame 108 and housing 110 move toward each other and closer together, which moves the upper and lower endplates 102A, 102B, 104A, 104B away from each other both vertically V and horizontally H1, and the lateral expansion wedges 106A, 106B away from each other horizontally H2, to expand the expandable interbody spacer 100.

During movement frame 108 and housing 110 toward each other, the single-angle ramps 126 on the frame 108 and housing 110 engage angled ramp ends and laterally move the lateral expansion wedges 106A, 106B, the upper and lower endplates 102A, 102B, 104A, 104B and vertical expansion shuttles 116A, 116B. During the lateral movement, the vertical expansion shuttles 116A, 116B engage and horizontally move the upper and lower endplates 102A, 102B, 104A, 104B.

The design of the ramps between the components allows the upper endplates 102A, 102B to vertically move H away from the lower endplates 104A, 104B, and the right upper and lower endplates 102A, 104A to horizontally move W away from the left upper and lower endplates 102B, 104B, thereby expanding the expandable interbody spacer 100 both vertically and horizontally from the collapsed state (FIG. 12A) to the expanded state (FIG. 12B).

In the collapsed state the expandable interbody spacer 100 has a first height H1 and first width W1. When the screw 108 is rotated in a first direction, the frame 104 and housing 106 start moving toward each other and the endplates expand to a second height H2 and second width W2. The expandable interbody spacer 100 does not have to be completely extended to H2 and can be stopped anywhere between H1 and H2, depending on the expansion needed between the adjacent vertebrae.

In the expanded state the expandable interbody spacer 100 includes a central opening that may be filled with materials, such as bone graft, allograft, Demineralized Bone Matrix ("DBM") or other suitable materials.

The upper and lower endplates 102A, 102B, 104A, 104B may include surface features or treatment configured to promote bone growth that engage the bone. For example, the surface may be a textured surface or roughened surface to promote bone integration or the surface may use a coating or be chemically etched to form a porous or roughened surface. In some embodiments the surface may include teeth. Each of the upper and lower endplates 102A, 102B, 104A, 104B may use the same surface feature or different surface feature.

The expandable interbody spacer 100 components may be fabricated from any biocompatible material suitable for implantation in the human spine, such as metal including, but not limited to, titanium and its alloys, stainless steel, surgical grade plastics, plastic composites, ceramics, bone, or other suitable materials. In some embodiments, surfaces on the components may be formed of a porous material that participates in the growth of bone with the adjacent vertebral bodies. In some embodiments, the components may include a roughened surface that is coated with a porous material, such as a titanium coating, or the material is chemically etched to form pores that participate in the growth of bone with the adjacent vertebra. In some embodiments, only portions of the components be formed of a porous material, coated with a porous material, or chemically etched to form a porous surface, such as the upper and lower surfaces that contact the adjacent vertebra are roughened or porous.

The expandable interbody spacer 100 may also be used with various tools, such as inserter tools, deployment tools and/or removal tools. The tools may include various attachment features to enable percutaneous insertion of the expandable interbody spacer 100 into the patient. For example, the tools may include arms or clamps to attach to the cutouts or other openings, slots or trenches of the drive mechanism. The tools may also include an actuation device to couple with the proximal section of the screw 112. Once the expandable interbody spacer 100 has been inserted and positioned within the intervertebral space between two vertebrae with the insertion tool, the deployment tool may actuate to deploy and expand the expandable interbody spacer 100 by applying a rotational force to screw 112.

In operation, the expandable interbody spacer 100 may be inserted into the intervertebral disc space between two vertebrae using an insertion tool. In some cases, the disc space may include a degenerated disc or other disorder that may require a partial or complete discectomy prior to insertion of the expandable interbody spacer 100. The deployment tool may engage with the proximal end of the expandable interbody spacer 100. As the deployment tool applies the rotational force, the expandable interbody spacer 100 gradually expands as described above. In some cases, the expandable interbody spacer 100 may need to be removed with a removal tool.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. An expandable interbody spacer for placement between adjacent vertebrae comprising:
   a frame having lateral frame ramps and lateral frame slots;
   a housing having lateral housing ramps and lateral housing slots;
   a drive screw configured to axially translate the frame and housing;
   left and right lateral expansion wedges having lateral wedge ramps slidingly engaged with the lateral frame ramp and the lateral housing ramp;
   left and right proximal vertical expansion shuttles having lateral protrusions and proximal vertical shuttle ramps, the lateral protrusions slidingly coupled to the lateral housing slots and proximal vertical shuttle ramps coupled to left and right lateral expansion wedges;
   left and right distal vertical expansion shuttles having lateral protrusions and distal vertical shuttle ramps, the lateral protrusions slidingly coupled to the lateral frame slots and distal vertical shuttle ramps are coupled to the left and right lateral expansion wedges;
   left and right upper endplates having proximal and distal vertical endplate ramped features, the proximal vertical endplate ramped features are slidingly engaged with the proximal vertical shuttle ramps and the distal vertical endplate ramped features are slidingly engaged with the distal vertical shuttle ramps;
   left and right lower endplates having proximal and distal vertical endplate ramped features, the proximal vertical endplate ramped features are slidingly engaged with the proximal vertical shuttle ramps and the distal vertical endplate ramped features are slidingly engaged with the distal vertical shuttle ramps;
   wherein movement of the drive screw in a first direction is configured to axially translate the frame and housing toward each other inducing lateral expansion of the left and right lateral expansion wedges to move away from each other, which also moves the left and right proximal vertical expansion shuttles away from each other, while simultaneously, axially translating the proximal vertical expansion shuttles toward the distal vertical expansion shuttles, inducing both lateral expansion and vertical expansion of the upper and lower endplates from a collapsed state to an expanded state.

2. The expandable interbody spacer of claim 1, wherein movement of the drive screw in a second direction is configured to move the frame and housing away from each other and collapse the expandable interbody spacer to the collapsed state.

3. The expandable interbody spacer of claim 1, wherein the frame and housing both contain single-angle ramps intended to induce lateral expansion of the right and left lateral expansion wedges during axial translation of the frame and housing.

4. The expandable interbody spacer of claim 1, wherein the right and left upper and lower endplate ramped features are single-angle rails and the proximal and distal vertical shuttle ramps are single-angle rails, the endplate ramped single-angle rails being slidingly engaged with the vertical shuttle single-angle rails to induce vertical expansion of the right and left upper and lower end plates during axial translation of the frame and housing.

5. The expandable interbody spacer of claim 1, wherein the distal vertical shuttle ramps and proximal vertical shuttle ramps have the same angle so a distal end and a proximal end of the upper and lower endplates have the same rate of vertical expansion.

6. The expandable interbody spacer of claim 1, wherein the distal vertical shuttle ramps have a different angle than proximal vertical shuttle ramps to induce different rates of vertical expansion between the proximal and distal ends of the upper and lower endplates.

7. The expandable interbody spacer of claim 6, wherein varying the vertical expansion rate can be utilized to induce lordosis within the implant as it is expanded.

8. The expandable interbody spacer of claim 1, wherein the right and left upper and lower endplate ramped features fit through upper and lower openings in the right and left lateral expansion wedges.

9. The expandable interbody spacer of claim 1, wherein the proximal and distal vertical expansion shuttles are captured within inward facing slots of the lateral expansion wedges proximate the upper and lower openings.

10. An expandable interbody spacer for placement between adjacent vertebrae comprising:
    a distal frame having upper and lower angled ramps and lateral slots;
    a proximal housing having upper and lower angled ramps and lateral slots a drive screw coupled to the distal frame and proximal housing being configured to translate the distal frame proximally or distally toward the proximal housing;
    right and left lateral expansion wedges having angled ramp ends configured to slidingly couple with the upper and lower angled ramps of the frame and housing;
    right and left vertical expansion shuttles positioned within upper and lower openings of the right and left lateral expansion wedges, the right and left vertical expansion shuttles having rail protrusions slidingly coupled to the lateral slots of the frame and housing;

left and right upper endplates having ramped features extending from a bottom surface configured to fit in the upper opening of the right and left lateral expansion wedges and slidingly engage vertical ramps of the left and right vertical expansion shuttles;

left and right lower endplates having ramped features extending from a top surface configured to fit in the lower opening of the right and left lateral expansion wedges and slidingly engage vertical ramps of the left and right vertical expansion shuttles;

wherein movement of the drive screw in a first direction is configured to move the frame and housing toward each other and the upper and lower angled ramps engaging the angled ramp ends and laterally expand the lateral expansion wedges, while simultaneously the vertical expansion shuttles axially translate toward each other, inducing vertical expansion of the upper and lower endplates to expand the interbody spacer from a collapsed state to an expanded state.

11. The expandable interbody spacer of claim 10, wherein movement of the drive screw in a second direction is configured to move the frame and housing away from each other and collapse the expandable interbody spacer to the collapsed state.

12. The expandable interbody spacer of claim 10, wherein the frame and housing both contain single-angle ramps intended to induce lateral expansion of the right and left lateral expansion wedges during axial translation of the frame and housing.

13. The expandable interbody spacer of claim 10, wherein the right and left upper and lower endplate ramped features are single-angle rails and the right and left vertical shuttle ramps are single-angle rails, the endplate ramped single-angle rails being slidingly engaged with the vertical shuttle single-angle rails to induce vertical expansion of the right and left upper and lower end plates during axial translation of the frame and housing.

14. The expandable interbody spacer of claim 10, wherein the distal vertical shuttle ramps and proximal vertical shuttle ramps have the same angle so a distal end and a proximal end of the upper and lower endplates have the same rate of vertical expansion.

15. The expandable interbody spacer of claim 10, wherein the distal vertical shuttle ramps have a different angle than proximal vertical shuttle ramps to induce different rates of vertical expansion between the proximal and distal ends of the upper and lower endplates.

16. An expandable interbody spacer for placement between adjacent vertebrae comprising:
a frame having lateral expansion features;
a housing having lateral expansion features;
a drive mechanism configured to axially translate the frame and housing;
left and right lateral expansion wedges having lateral expansion features slidingly engaged with the frame and housing lateral expansion features;
left and right proximal shuttles with vertical expansion features being coupled to the housing lateral expansion features and the left and right lateral expansion wedges;
left and right distal expansion shuttles with vertical expansion features being coupled to the frame lateral expansion features and the left and right lateral expansion wedges;
left and right upper endplates having proximal and distal vertical expansion features, the proximal vertical expansion features slidingly engaged with the proximal shuttle vertical expansion features and the distal vertical expansion features configured to slidingly engage the distal shuttle vertical expansion features;
left and right lower endplates having proximal and distal vertical expansion features, the proximal vertical expansion features configured to slidingly engage the proximal vertical shuttle expansion features and the distal vertical expansion features configured to slidingly engage the distal vertical shuttle expansion features;
wherein movement of the drive mechanism in a first direction is configured to axially translate the frame and housing toward each other inducing lateral expansion of the left lateral expansion wedge to move away from the right lateral expansion wedge, which also moves the left proximal vertical expansion shuttles away from the right distal expansion shuttle to move, while simultaneously axially translating the left and right proximal vertical expansion shuttles toward the left and right distal vertical expansion shuttles, inducing both lateral and vertical expansion of the upper and lower endplates from a collapsed state to an expanded state.

17. The expandable interbody spacer of claim 16, wherein lateral expansion features of the frame and housing and the lateral expansion features of the left and right lateral expansion wedges include laterally angled ramps.

18. The expandable interbody spacer of claim 16, wherein vertical expansion features of the proximal and distal expansion shuttles and upper and lower endplates include vertically angled rails.

19. The expandable interbody spacer of claim 18, wherein the distal vertical angled rails and the proximal vertically angled rails have a same angle so a distal end and a proximal end of the upper and lower endplates have the same rate of vertical expansion.

20. The expandable interbody spacer of claim 18, wherein the distal vertical angled rails and the proximal vertically angled rails have a different angle to induce different rates of vertical expansion between the proximal and distal ends of the upper and lower endplates.

* * * * *